US010420680B2

(12) United States Patent
Schmitz (10) Patent No.: US 10,420,680 B2
(45) Date of Patent: Sep. 24, 2019

(54) METHOD FOR SEPARATING PORTIONS FROM A WEB AND RECOMBINING THESE ONTO THE WEB MACHINE-DIRECTIONALLY OFFSET (71) Applicant: Concepts for Success (C4S), Euskirchen (DE)

(72) Inventor: Christoph Schmitz, Euskirchen (DE)

(*) Notice: Subject to any disclaimer, the term of this patent is extended or adjusted under 35 U.S.C. 154(b) by 0 days.

(21) Appl. No.: 15/509,471

(22) PCT Filed: Sep. 11, 2015

(86) PCT No.: PCT/EP2015/070780
§ 371 (c)(1),
(2) Date: Mar. 7, 2017

(87) PCT Pub. No.: WO2016/038170
PCT Pub. Date: Mar. 17, 2016

(65) Prior Publication Data
US 2017/0239100 A1 Aug. 24, 2017

(30) Foreign Application Priority Data

Dec. 9, 2014 (GB) .................................. 1416135.0
Feb. 26, 2015 (GB) .................................. 1503278.2

(51) Int. Cl.
*A61F 13/00* (2006.01)
*B65H 37/00* (2006.01)
*A61F 13/15* (2006.01)
*B65H 37/04* (2006.01)

(52) U.S. Cl.
CPC .. *A61F 13/15756* (2013.01); *A61F 13/15723* (2013.01); *A61F 13/15764* (2013.01); *B65H 37/04* (2013.01); *A61F 2013/15821* (2013.01); *B65H 2801/57* (2013.01)

(58) Field of Classification Search
CPC .......... A61F 13/00; A61F 13/10; A61F 13/15; A61F 13/15; A61F 13/157; A61F 13/157; A61F 13/1575; A61F 13/1575; A61F 13/15756; A61F 13/1572; A61F 13/1572; A61F 13/15723; A61F 13/1576; A61F 13/1576; A61F 13/15764; B65H 37/00; B65H 37/04
See application file for complete search history.

(56) References Cited

U.S. PATENT DOCUMENTS

| 6,544,375 B1* | 4/2003 | Schmitz | A61F 13/15593 156/264 |
| 2014/0102851 A1* | 4/2014 | Papsdorf | A61F 13/15764 198/411 |

FOREIGN PATENT DOCUMENTS

| EP | 396050 A2 | 11/1990 |
| EP | 539032 A1 | 4/1993 |
| EP | 652175 A1 | 10/1995 |
| EP | 797970 A2 | 2/1997 |
| WO | 1996024319 A1 | 8/1996 |
| WO | 1996031180 A1 | 10/1996 |
| WO | 1998025767 A1 | 6/1998 |

(Continued)

*Primary Examiner* — Jacob T Minskey
*Assistant Examiner* — Matthew Hoover
(74) *Attorney, Agent, or Firm* — Robert A. Haupt (57) ABSTRACT

The present invention is an equipment and a method for handling web materials, in particular for recombining portions as are cut out from an essentially continuous web material machine-directionally offset with this web.

11 Claims, 10 Drawing Sheets (56) References Cited

FOREIGN PATENT DOCUMENTS

WO 2008141658 A1 11/2008
WO 2015036561 A1 3/2015

* cited by examiner

METHOD FOR SEPARATING PORTIONS FROM A WEB AND RECOMBINING THESE ONTO THE WEB MACHINE-DIRECTIONALLY OFFSET

FIELD OF THE INVENTION

The present invention relates to a method and equipment for the handling of web materials, such as essentially continuous webs of plastic films, textiles, non-wovens, or papers, or the like, and to the handling of discrete parts or portions of such webs, which are to be recombined with such webs at a machine-directionally offset positioning.

BACKGROUND

Web materials, such as films, papers, woven or nonwoven materials are broadly used and handled in the industry. Often such webs are trimmed such that holes or apertures are created, which are discarded, whilst other materials, are added to the web.

It is a well-known technology to apply relatively short pieces of a second material to a first web, when the second material is cut from an essentially endless supply and the pieces of the second material are positioned in a spaced arrangement on the first web.

In a first approach, the second material is provided as an essentially continuous material running at a direction perpendicular to the first web, and the cut pieces are positioned cross-directionally onto the first web, see e.g. EP0652175A1. In this method, for the moment of the combination of the web and the pieces, there should be no speed mismatch and thus there is a strong limitation with regard to the manufacturing speed, or other complex measures must be taken.

In a second approach, the second material is applied when running in essentially the same direction as the first material, using the "cut and space" principle. This method is also referred to as "cut and slip" method, as it requires the shorter material to be accelerated to the speed of the first web.

Yet a further approach is to avoid a speed mismatch by use of varying speed support, such as well-known server motor driven rolls.

It is also known to separate a web along a predominantly longitudinally extending line, such as a meandering line, to machine-directionally offset one portion versus the other, optionally reposition the web path of one of these portions such that the previously outward longitudinal side margins are now positioned towards each other and the separation line forms lateral margins, see e.g. WO2008/141658A1, EP0539032A1, EP0797970A2, EP0396050A2, WO1998/025767A1, or WO1006/031180A1.

However, there is still a need for a simple and reliable method for applying discrete pieces or portions of a web material to other portions of the same web, in particular, if this web is of low strength or has elastic properties.

SUMMARY

In a first aspect, the present invention is a method for repositioning and recombining separated portions of a web material machine-directionally offset. The method comprises the steps of:
1) providing
   a. a web material exhibiting lateral side margins;
   b. a separation unit for forming at least partially separated portions in predetermined regions of the web material;
   c. a transfer unit for transferring the at least partially separated portions of the web material;
   d. a web guide unit for the web material;
   e. a combination unit;
2) feeding the web material along a first web path to the separation unit;
3) applying an essentially continuous separation line, thereby creating a series of at least partially separated portions in predetermined regions of the web material in the separation unit,
   such that the web material remains essentially continuous along its side margins,
   whilst the at least partially separated portions of the web material are circumscribed by the essentially continuous separation line or an essentially cross-directionally extending connection and fold fine that connects end points of the separation line, optionally forming an essentially disconnected series of separated portions;
4) guiding the web material by the web guide unit along a second part of the essentially continuous web path from the separation unit to the combining unit;
5) transferring at least a leading portion of the at least partially separated portions by the transfer unit along a separated portions path, differing from the second part of the web path;
6) recombining the web material and separated portions in the combination unit;
whereby in the method the separated portions are positioned machine-directionally offset relative to the predetermined regions from which they are separated.

When the at least partially separated portions are fully separated portions, the method may further comprise the steps of
1f) providing a reorientation unit for the fully separated portions;
7) reorienting the fully separated portions along the separated portions path.

Optionally, the fully separated portions may be cross-directionally offset relative to the predetermined regions.

When the at least partially separated portions are partially separated portions, step 5) may be executed such that
the leading portion of the partially separated portion is temporarily attached to the transfer unit,
wherein further a fold line is created at the trailing edge of the separated portions, and
wherein the partially separated portion is released from the transfer unit and positioned on the web material after being rotated around a y-directionally extending axis.

The method may further comprise the steps of
8) providing a further material;
9) combining the further material with the separated portions or the web material such that it contacts either of the materials or both.

The method may further comprise the steps of
1g) providing a connection unit;
10) connecting the separated portions to the web, optionally also to the further material, preferably by melt fusion bonds, more preferably ultrasonically formed bonds.

Preferably, at least two units selected from the group consisting of the transfer unit, the separation unit, the reorientation unit, the combination unit, and the connection unit are essentially unitary.

In another aspect, the present invention is a method for the manufacture of disposable absorbent articles, which comprises the method for repositioning and recombining separated portions of a web material machine-directionally offset, wherein the separated portions may be side panel pieces adapted to form a waist hoop during use.

In yet another aspect, the present invention is an equipment for the repositioning of portions of a web material machine-directionally offset to the web material from which they are separated. The equipment comprises
  a) a web supply unit for supplying an essentially continuous web material, the web exhibiting predominantly longitudinally extending side margins;
  b) a separation unit for at least partially separating portions of the web material whilst maintaining the web material as continuous web material;
  c) a combination unit for recombining separated portions of the web material with the web material,
  d) a transfer unit a transfer unit for transferring at least a leading portion of the at least partially separated portions of the web material along a separated portions path;
  e) a guide unit for transferring the web material from the separation unit to the combination unit along a second web path.

Therein, the separated portions path and the second web path exhibit an essentially different path length. Optionally, the equipment may further satisfy at least one of the conditions selected from the group consisting of
  m) the separation unit and the transfer unit comprise a common element;
  n) the transfer unit and the combination unit comprise a common element.

The equipment may further comprise one or more of elements selected from the group consisting of
  f) a reorientation unit for changing the orientation of the separated portions;
  g) a connecting unit for connecting the separated portions and the web material in or after the combination unit.

Optionally, the equipment may further satisfy at least one of the conditions selected from the group consisting of
  o) the reorientation is unitary with the transfer unit;
  p) the connecting unit is unitary with the combination unit.

BRIEF DESCRIPTION OF THE FIGURES

In all figures, same numerals denote identical or corresponding features.

DETAILED DESCRIPTION

"Comprise," "comprising," and "comprises" is an open-ended term that specifies the presence of what follows, e.g. a component, but does not preclude the presence of other features, elements, steps or components known in the art, or disclosed herein. Within the present context, the term "predominantly extending in one direction" means that a line, a cut, or a separation line has a projection onto this direction that is larger than its projection onto the direction perpendicular thereto.

In a first aspect, the present invention is a method for repositioning fully or at least partially separated portions of a continuous web material machine-directionally offset to the web material from which they are separated, and in a second aspect an apparatus for executing such a process.

The present invention is particularly suitable for being used in continuous production processes, and even more so when such processes are operated at high production speed, that may exceed 500 m/min.

The method according to the present invention is particularly useful for the manufacturing of hygiene articles, such as, but not limited to, disposable baby diapers, training pants, adult incontinence articles, feminine hygiene articles, disposable underwear and the like. "Disposable" is used herein to describe articles that are generally not intended to be laundered or otherwise restored, i.e., they are intended to be discarded after use and, preferably, to be recycled, composted or otherwise disposed of in an environmentally compatible manner. It should be noted, that disposable articles may be used several times, such as wearing disposable underwear over several days, or re-using disposable absorbent articles if these have not been loaded at the first use occasion. It should also be noted, that disposable articles may be washable, and may actually be washed for a limited number of wash-cycles, typically not more than ten wash cycles.

The term "web material" refers to an essentially endless material in one direction, i.e. the longitudinal extension, or the length, or the x-direction in Cartesian coordinates relative to the web material. Often, though not necessarily, the web materials will have a thickness dimension (i.e. the z-direction) which is significantly smaller than the longitudinal extension (i.e. in x-direction). The webs exhibit lateral side margins and often, though not necessarily, the width of web materials (the y-direction) will be significantly larger than the thickness, but less than the length. Often, though not necessarily, the thickness and the width of such materials is essentially constant along the length of the web. Such web materials may be without intending any limitation, cellulosic fibre materials, tissues, films, woven or non-woven materials and the like. Typically, though not necessarily, web materials are supplied from a web supply unit in roll form, or on spools, or in a folded state in boxes. The individual deliveries may then be spliced together to form the essentially endless structure. A web material travels through process steps or an equipment along a web path along the machine direction of the process step or equipment, which is typically aligned with the longitudinal extension or x-direction of the web. A web material may be composed of several sub-web materials, such as—without limitation—being a multilayer non-woven, coated tissue, non-woven/film laminate. Also, two or more sub-web materials may be positioned aligned next to each other along the machine direction. Such sub-webs may be of the same type, or be different, such as by differing in composition, thickness, basis weight, or physical, including mechanical or chemical treatment of the sub-web materials. A particular execution may be a web material comprising elastic and non-elastic sub-web materials in a side by side arrangement along the machine direction, whereby the sub-web materials may be combined to form the web material prior to or concurrently with process steps according to the present invention. Web materials may comprise other materials, such as added particles, hydrophilizing agents and the like.

The terms "separating", "separated", or related expressions, in particular "separated portions", as well as the terms "cut", "cutting", offcut, or "cut-out" refer to the excising of portions from predetermined discrete regions of a web material to form separated portions. Such methods are and respective equipment is well-known in the art, such as when using die cutters, wherein cutting blades operate against an anvil, or water jet cutting, or laser cutting or the like and thus not limited to "cutting" in the narrow sense of a separation technology employing one or more blades or dies. At least initially and until a reorientation, the separated portions exhibit the same directionality as the web material, i.e. a machine or x-direction, a cross machine or y-direction and a thickness or z-direction. The separated portions may be executed as fully separated portions, for which a separation line circumscribes the portions, or as partially separated portions. In the latter case, the separation line is not a closed line, like a circle, but exhibits a first and a second end point. Within the present context, these endpoints are cross-directionally offset and the connection line between these endpoints extends essentially cross-directionally. Then, the partially separated portion may be lifted from the plane of the web and may be rotated along a y-directionally axis by being folded along the cross-directional connection or fold line.

Within the present context, the essentially continuous web material may be considered a sequence of individual web pieces. In the beginning of the process, such pieces may not be discernible and be delimited by invisible demarcation lines only, and sequentially following pieces may be physically separated further downstream, i.e. in an additional process step within or after the method according to the present invention. Typically, though not necessarily, sequentially following pieces have the same length.

Each of these pieces comprises at least one predetermined region, from which material is separated out by a separation unit. In one execution, parts of said separated out material may be discarded as trim, whilst one or more portions of said separated material are intended to be recombined in a combination unit with the web material at a machine-directionally offset position relative to the predetermined region from which they are removed. In another and often preferred execution, all of the separated material, i.e. all the separated portions or the offcut are recombined with the web material at a machine directionally offset position. In yet a further execution in the context of partially separated portions, the originally leading portion of the partially separated portion may become the trailing portion, when overlaying the web material after being rotated around a y-directional axis.

The term "combined" or "recombined" is intended to refer to any predetermined relative z-directional positioning of the separated portions and the web material to each other in a direct or indirect contact. For example, the separated portions may be directly placed on either side or surface of the web material, or there might by a further material positioned between them, for example a further web material or pieces thereof, or an adhesive layer, or the like.

Either of the fully or partially separated portions and the web material may undergo certain treatment steps before they are combined again, for example, they may be folded, or stretched, or cross-directionally displaced relative to each other, or treated with another material, such as an adhesive or glue.

The separated portions and the still continuous web, from which these are separated, travel preferably both at unchanged overall process speed—along different process paths before being combined again. The web material is delivered along a first part of the web path to the separation unit and along a second part of the web path from the separation unit to the combination unit The separated portions are delivered along a separated portions path from the separation unit to the combination unit. In case of the fully separated portions, these are transferred from the separation unit via a transfer unit to the combining unit, whilst the second part of the web path of the continuous web runs via a guide unit, such as a guide roll or rod, which is different and typically longer than the path of the separated portions via a transfer unit. In the case, that the second web path is longer than the separated pieces path, the separated portions will be positioned machine-directionally before the predetermined regions from which these were separated. In case of the partially separated portions, the leading part of the portion will be temporarily attached to the transfer unit and follows the separated portion path, whilst the trailing part of the partially connected portion is still connected to the web material along the connecting line, which extends essentially cross-directionally and then forms a folding line. Thusly, the partially separated portion is z-directionally pulled out of the plane of the web when the path of separated portion diverges from the second part of the web path.

Within the present context, the second web path and the separated portion paths start and end at the point of separation in the separation unit and the point of recombination in the combination unit, respectively.

In an optional and often preferred execution of the present invention, the separated portions may change their orientation along the separated portions path by an optional reorientation unit. In a first variant, this change in orientation of a fully separated portion may be a rotation around a z-directional axis, such that for a 180° rotation a leading margin of a separated portion becomes a trailing margin. Whilst the rotation may be at any angle of rotation, the 180° angle is preferred. Rotating web material pieces and the related equipment is well known in the art, such as described in US2014/0102851, to which express reference is made for the rotating equipment and process. For example, a transfer unit may comprise reorientation units such as support plates for the separated portions that are rotatably mounted around an axis, which may be z-directionally oriented or slightly angled thereto. Optionally the support plates may be equipped with holding means for affixing temporarily the separated portions on the support plates, such as vacuum suction. Optionally, the support plates may be translatorily moveable z-directionally.

Another way of achieving a change in orientation can be the flipping of the fully separated portions, such that longitudinally extending margins are changed and simultaneously a first x-y-extending surface of the separated portions that was e.g. formerly upwardly oriented becomes downwardly oriented after the flipping.

In case of partially separated portions, the reorientation is achieved by the rotation around a y-directional axis as described in the above.

In addition to machine-directional offsetting, and optionally reorienting the separated portions, the fully separated portions may also be cross-directionally offset compared to the continuous web material. This may be achieved by dislocating the web material cross-directionally in course of the second web path, as may be achieved by angled s-bars as being well known in the art. It may also be achieved concurrently with the reorientation of the separated portions, such as when the rotating axes for the support plates are not positioned centrally but laterally thereof.

It should be noted that the repositioning of the separated portions can be done such that they extend over two web material pieces, i.e. over a virtual demarcation line between these, and then may be separated into sub-portions by the downstream separation step of separating the web into individual pieces. Also, the repositioning can be such that separated regions are combined with a different web piece as they are separated from, such as can be achieved by extending the web path of the continuous web material further.

Typically, the separated portions or sub-portions are connected to the web material directly upon the combining or thereafter in a connecting unit, as may be integral with the combination unit, or which may be separate and positioned after the combination unit in the direction of the web path. Such a connecting can be achieved by any conventional means, such as application of adhesives prior to the combining, or preferably by melt fusion bonding, such as ultrasonic bonding. In other cases, separated portions may be first connected to another web material, and thereafter to the web material from which they were separated.

At least some of the process units for executing the present invention may optionally, and often preferably, be unified to form a single unit, for example, an anvil of the separation unit may function as the transfer unit, and/or the transfer unit may be a part of the combination unit.

The principles of the present invention are now further explained by referring to the figures, which should not be seen limiting in any way.

Figure 1A:
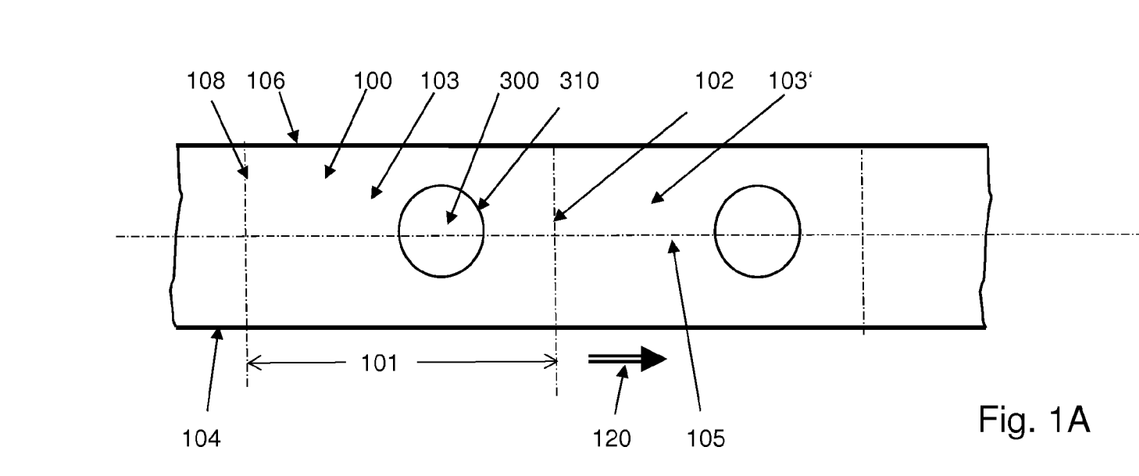
FIGS. 1A and B depict schematically how a separation portion is repositioned on a web.
Figure 1B:
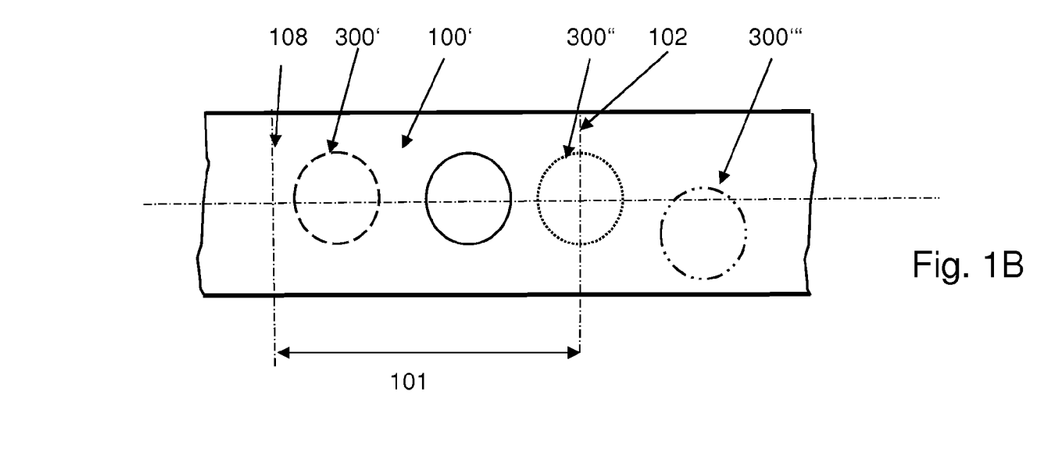
Figure 2:
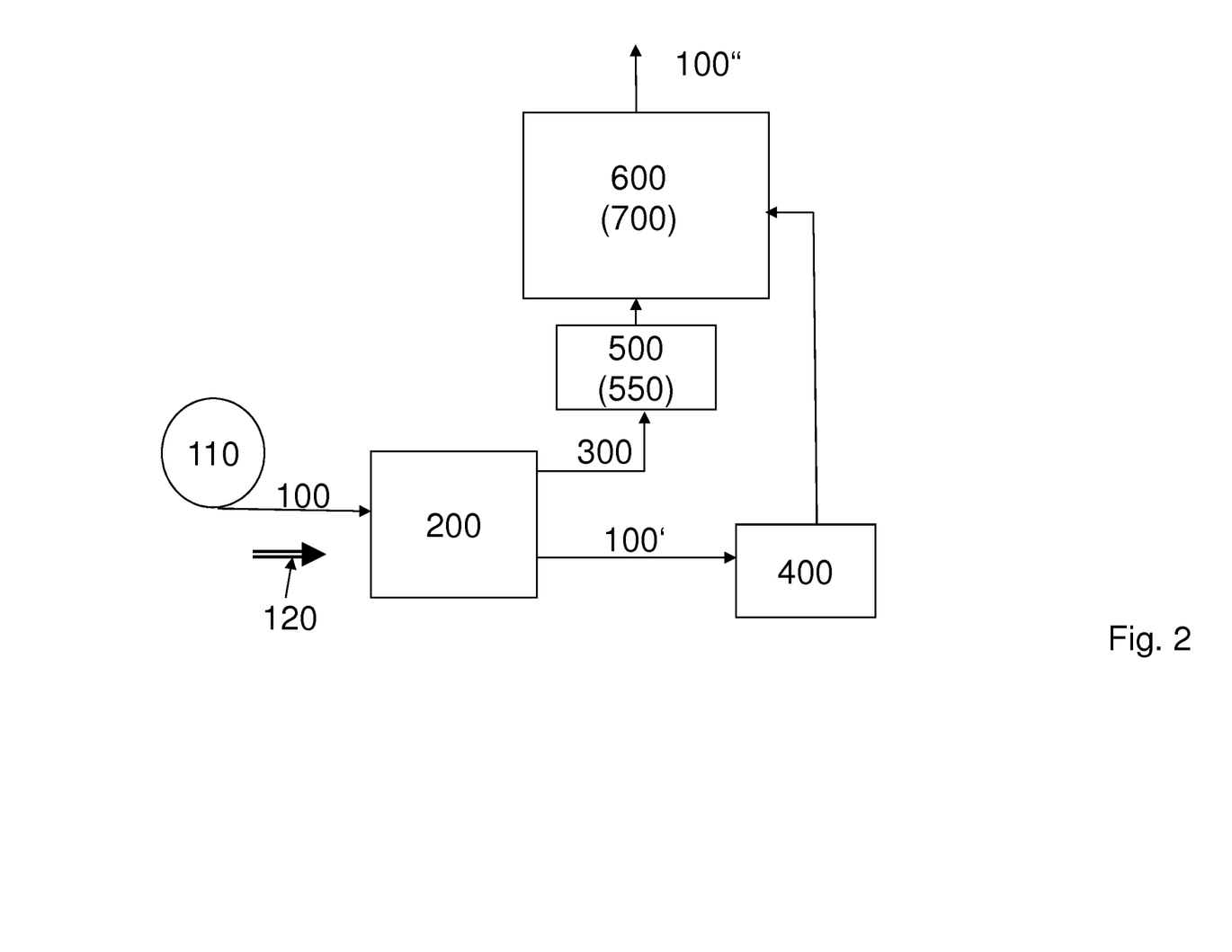
FIG. 2 depicts the process scheme for executing the present invention.

In FIGS. 1A, 1B, and 2A, a web material 100, exhibiting two longitudinally extending side margins 104 and 106, that are typically, though not necessarily, straight lines, is provided on a web material supply unit 110. It is fed at a web speed 120 to a separation unit 200, as may be a die cutting unit or other means for excising, such as laser or water cutting units or the like. On the separation unit 200, predetermined portions 300 of the web material are separated along a separation line forming the periphery of the separated portions, in this case fully separated portions. The shape of the predetermined separated portions is not particularly limiting, nor is their number, however at least one of the side margins 104, 106 of the web material should not be separated, such that the web material remains continuous. Along the overall length of the web material, there will be a repeating predetermined pattern of separated portions, corresponding to the repeating pieces 103, 103' of the web material with a predetermined pattern 310 of portions to be separated. Thus, in FIG. 1 one such web material piece 103 exhibiting a length 101 is indicated between a leading margin 102 and a trailing margin 108 along the direction of movement of the web as indicated by the web speed 120.

The leading and trailing margins may already be visible though typically they are not and thus may appear as invisible demarcation lines.

The fully separated portions 300 are then removed from the web material, which is now referred to as web material with separated portions removed 100'. This removal may be achieved by transferring the separated portions to a transfer unit 500, such as a transfer roll equipment with holding means, such as vacuum suction. It may also be achieved by removing the web 100', such as by having it run over a guide unit 400, as may be a conventional guide roll or turning bar. In analogy to the web path, the series of the discrete separated portions are moving along a separated portions path, which in the execution as shown corresponds to the surface of the rotating transfer unit 500. An optional reorientation unit 550, shown in FIG. 2 integral with the transfer unit may be used to alter the orientation of the separated portions. If the process is operated such that excess trim is generated, this trim may be removed from as a continuous trim web 325, or as individual trim pieces.

In the combination unit 600, the web material with separated portions removed 100' and the separated portions 300 are recombined. Reconnecting the separated portions and the web material after the recombination may be achieved in a separate connecting unit further downstream of the combining unit in the direction of the web path, or preferably in a connecting unit 700 integral with the combining unit 600.

As neither the web material with separated portions removed nor the separated portions have changed their speed, but the web material with separated portions removed 100' has been running over a predetermined and well and easily adjustable web path which is different and—as shown exemplarily—longer than the path of the separated portions, the positioning of the separated portions relative to their original position, which is now a cut-out portion in the web, has changed.

In FIG. 1B, the separated portions are shown to be repositioned in position 300' (the circumscribing perimeter being indicated by dashed line) or in position 300" (the perimeter being indicated by dotted line). It should be noted that for the second repositioning to 300", the separated portions will be separated into sub-portions by the final separation of the web into web pieces. As indicated by a further repositioning position 300'" (dash-double dotted line), the separated portions may be positioned cross-directionally offset from their predetermined region they are separated from. They may also be combined with different sequential piece(s) of the web material than the one they are separated from.

Figure 3:
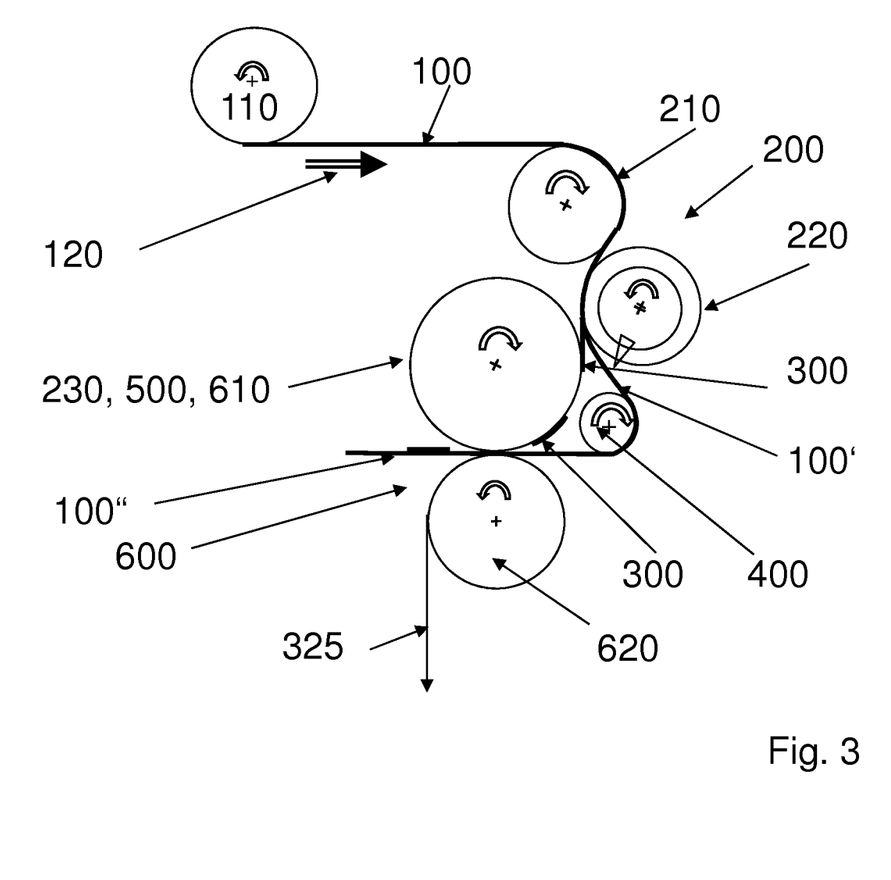
FIG. 3 depicts an equipment according to the present invention.

FIG. 3 exhibits exemplarily and for explanatory purposes an equipment arrangement according to the present invention. The equipment comprises a web supply unit 110, from which the web material 100 is transferred at a web speed 120 to a separation unit 200, here shown exemplarily with a guide roll 210, a die roll 220, and an anvil roll 230. The separation unit 200 separates the fully separated portion 300 from the continuous web material with separated portions removed and now indicated 100', which is guided by a guide unit 400 away from the anvil roll 230. As depicted, the anvil roll 230 is also operated as transfer drum 500, as well as one of the combination rolls 610, 620 of the combination unit, where the web material with separated portions removed 100' and the separated portions are recombined to form the web material with separated portions recombined 100", which may then be transferred to further processing steps, such as separating web pieces from the web.

It should be noted that for the purpose of easy explanation, the separated portions are described to be recombined with the web material essentially as they are, i.e. they are not treated or otherwise handled other than machine and/or cross-directionally displaced. Also, all separated and cut-out material is recombined, so in this exemplary presentation there is essentially no scrap generated.

Figure 4:
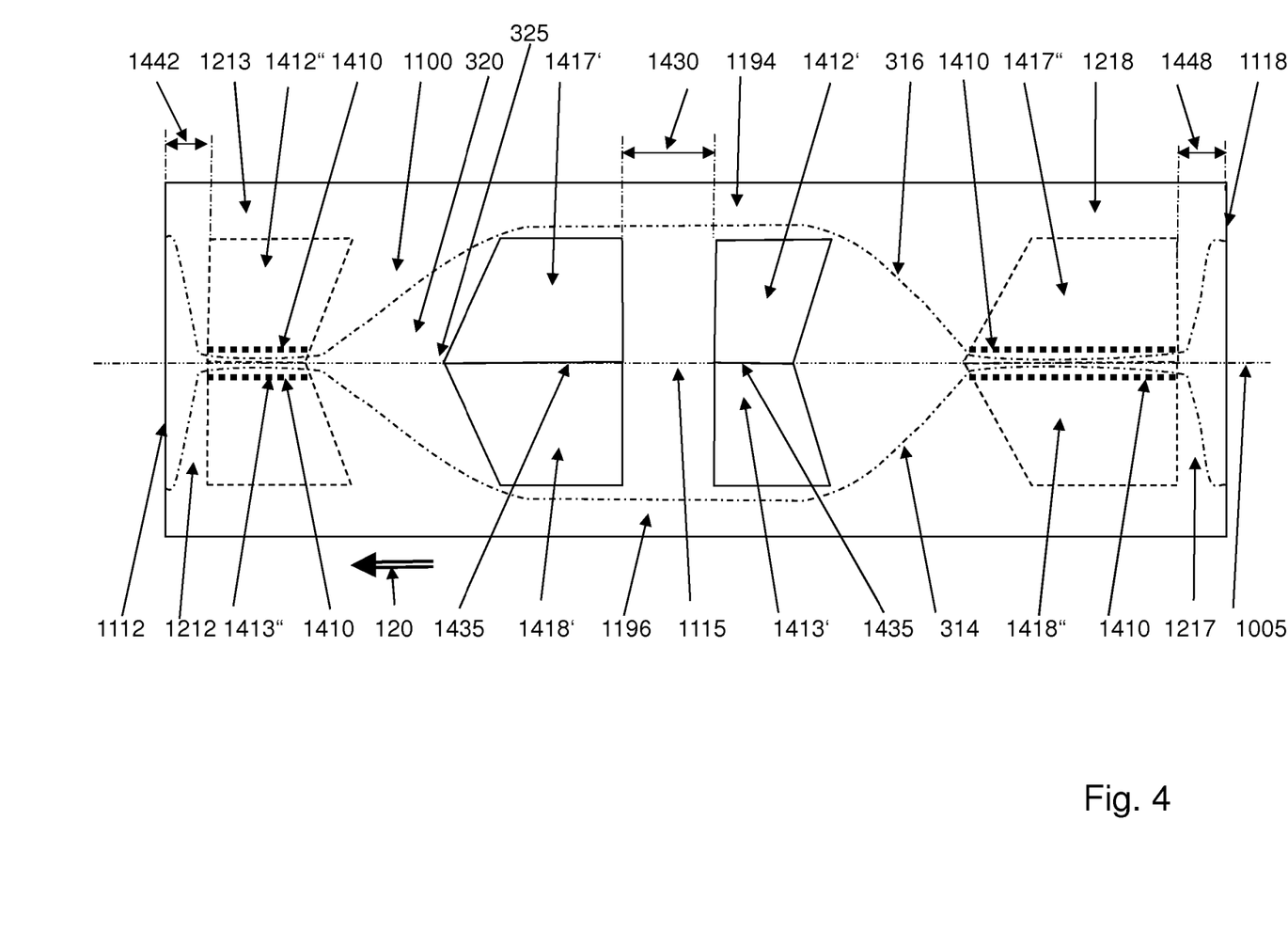
FIG. 4 depicts schematically an application of the present invention in the context of manufacturing and absorbent article.

In FIG. 4, a further exemplary execution for applying the present invention is shown. This refers to the manufacturing of absorbent articles to be worn on the lower torso of a wearer, such as diapers. Such articles typically comprise a topsheet positioned towards a wearer during use, a backsheet opposite thereof and an absorbent core there between. In order to hold the article on the wearer, such articles may further comprise side panels, which may further have side panel extension connected so as to allow forming a waist hoop around the waist of a wearer. Such articles and their manufacturing are well known in the art.

A particular method for the manufacturing of such articles is described in copending application PCT/EP2014/069538 (unpublished), to which express reference is made for the subject matter of forming side panels and in particular side panel extensions from a further backsheet material. In FIG. 4, the present invention is described for web material as may be represented by such a further backsheet that may form side panels on an article as well as side panel extensions that are cut out from the further backsheet and connected to the side panel portions. The further backsheet may be combined with further elements to form an absorbent article, in particular a backsheet and a topsheet (not shown).

The further backsheet 1100 as a continuous web material is shown with a first and a second end margin, that may correspond to a front or rear end margin of a web material piece 1112, and 1118, respectively, when travelling along a machine direction at a web speed 120, that may form the corresponding margins of adjacent further backsheet pieces (not shown), as discussed in the above. Two separation lines 314 and 316 are shown with dash-dotted lines, extending predominantly in the MD direction of the further backsheet and—for the example shown—symmetric to the longitudinal centre line 1005 (dash-double dotted line). This line separates a laterally inward piece 320 and two laterally outwardly positioned symmetric continuous pieces, which may form a first and a second front side panel of the article 1212, 1213, a first and a second rear side panel 1218, 1217, and longitudinally positioned there between a first and a second leg hoop 1194, 1196, which are positioned in the centre or crotch region 1115 of an article.

According to the present invention, side panel extension pieces may now be cut as separated portions or sub-portions thereof from the laterally inward piece 320. To this end, the side panel extension pieces are separated each around their full perimeter. This may be executed on a vacuum supported anvil drum 230, against which a die cutting unit 220 operates and performs the separation, as shown in FIG. 3. The four side panel extension pieces may have an arbitrary shape, limited by the space and design requirements for leg hoops and side panels. In the figure, the pieces are shown in solid lines as sub-portions of the inward piece 320 in the position prior to repositioning, namely first 1417' and second 1418', forwardly positioned sub-portions and first 1412' and second 1413' rearwardly positioned sub-portions. After repositioning, the sub-portions are positioned for functioning as side panel extension pieces 1417", 1418", 1412" and 1413", respectively, and shown with dashed lines. The repositioned side panel extensions may be connected to the corresponding side panels, here shown by connecting lines 1410. Prior to the repositioning, the sub-portions forming front side panel extension pieces are positioned rearwardly of the sub-portions forming the rear side panel extension pieces. The sub-portions for the front and rear side panel extension pieces are longitudinally separated by side panel extension MD-spacing 1430, which corresponds to the sum of the front side panel extension margin length 1442 and the rear side panel extension margin length 1448. First (1417', 1412') and second (1418', 1413') sub-portions are separated by a separation line 1435 essentially coinciding with the longitudinal centre line 1005, or by separate predominantly longitudinally extending separation lines (not shown). In this execution, only the sub-portions 1412', 1413', 1417' and 1418' forming the four side panel extension piece as indicated by the solid lines are repositioned, recombined and connected to the four corresponding side panels. Thus, a trim portion 325 of the inward piece 320 is not directly used in this design, and may be discarded, such as by being pulled away from the web material e.g. at anvil roll 620, FIG. 3.

Whilst the vacuum holds the sub-portions for forming the side panel extension pieces on the anvil drum, the remaining continuous part of the further backsheet material web 1110 is withdrawn from this drum towards a guide roll and back to the anvil drum, thereby creating a machine directional offset such that the rearwardly positioned sub-portions form front side panel extension pieces on a further backsheet piece, whilst the forwardly positioned sub-portions form rear side panel extension pieces of an adjacent, e.g. preceding further backsheet piece.

Figure 5:
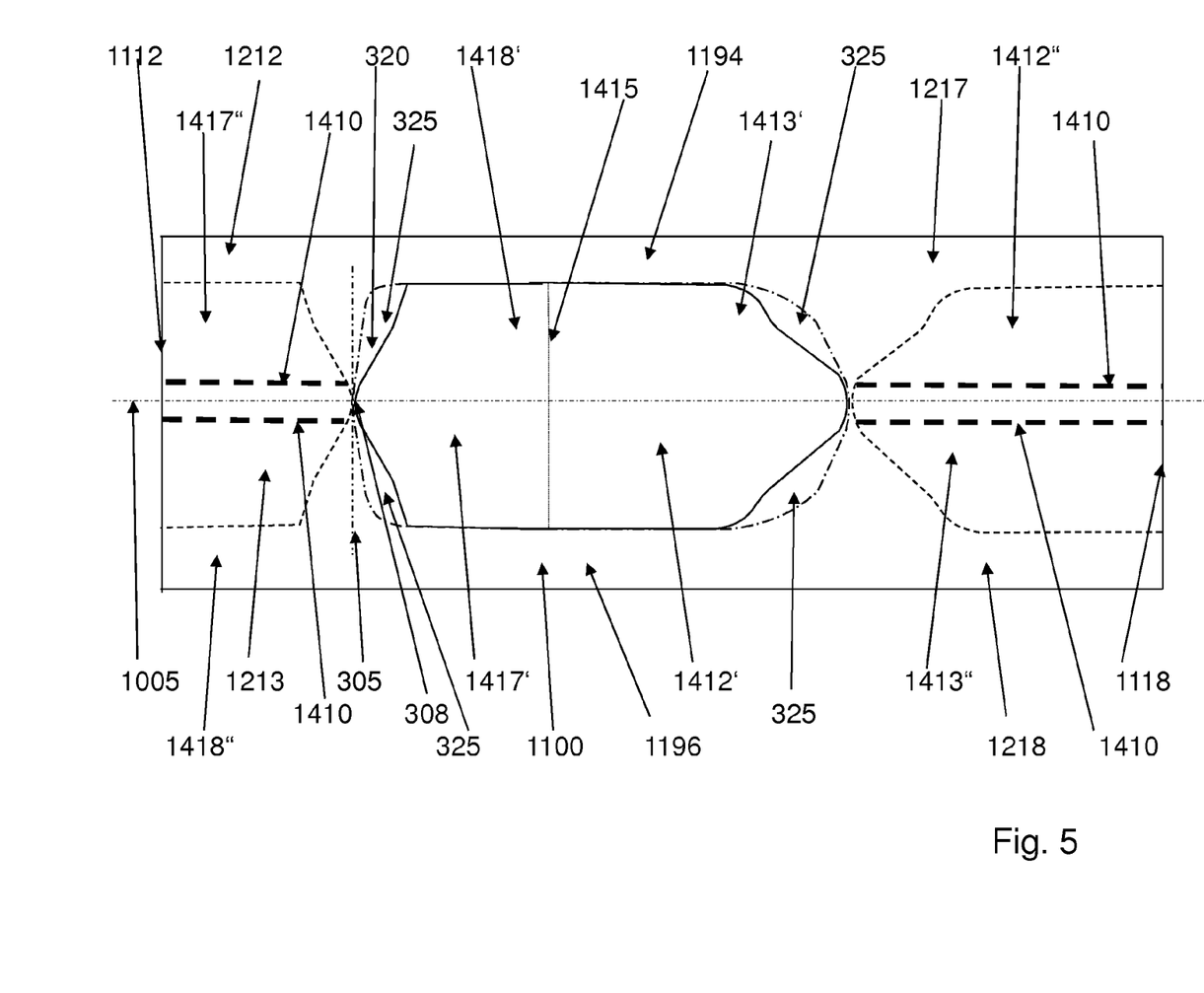
FIG. 5 depicts schematically an execution according to the present invention, wherein separated portions are recombined with the web after these have been reoriented.
Figure 10:
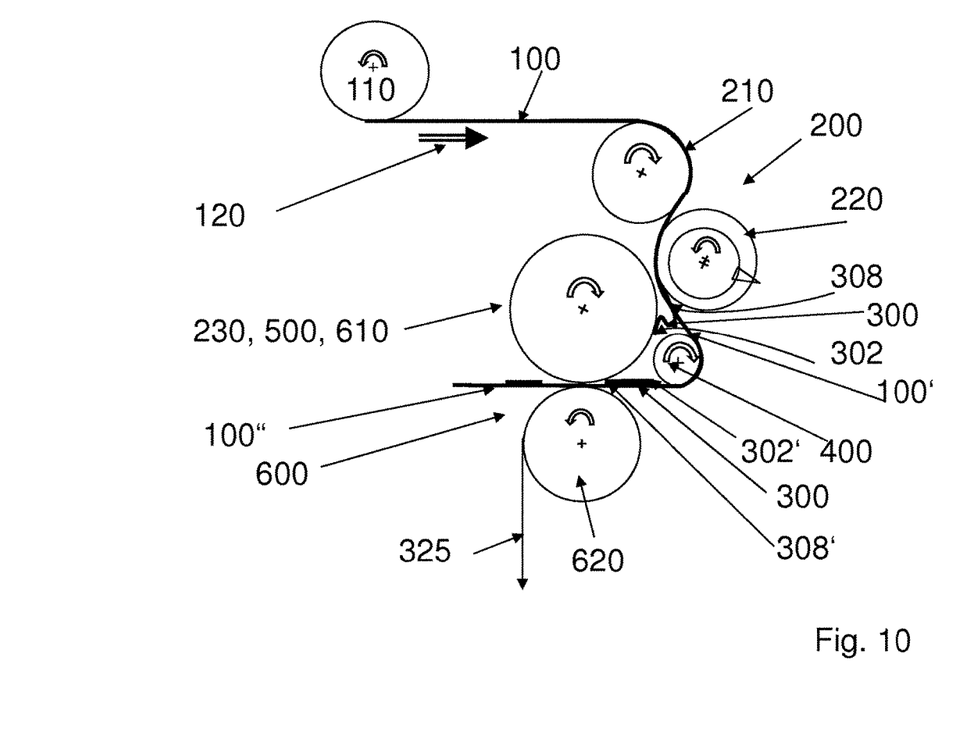
FIG. 10 depicts an alternative equipment according to the present invention.

FIG. 5 depicts another execution according to the present invention. In analogy to FIG. 4, a continuous web material is represented by a further backsheet 1100, exhibiting a first, e.g. a front, margin 1112 and a second, e.g. a rear, margin 1118, that may correspond to a front or rear end margin of a web material piece, a longitudinal centre line 1005, four side panel regions 1212, 1213, 1217, and 1218, as well as two leg hoop regions 1194 and 1196. An inward piece 320, demarcated by a dash-dotted line (partly coinciding with a solid line), comprises sub-portions for forming the side panel extension. The outer perimeter of these four sub-portions is shown as a solid line, whilst the four sub-regions 1412', 1413', 1417', and 1418' are shown separated from each other by the imaginary longitudinal centre line 1005 and a cross-directionally extending imaginary separation line 1415. They are further shown in a post reposition location as side panel extension pieces 1412", 1413", 1417", and 1418", respectively, with thin dashed lines. Connecting lines 1410 (thick dashed lines) connect the side panel extensions to the side panels. A reorientation of fully separated portions may be achieved by an additional 180° rotational move around a z-directional axis of the separated sub-portions as may be accomplished by a reorientation unit integral with the transfer unit. Such rotational moves are well known in the art, such as in US2014/0102851, to which express reference is made for the rotating equipment and process. As a skilled person will readily realize, the sub-portions are changing their "first-second" e.g. left-right, positioning. Also, the sub-portions which are positioned more forwardly prior to repositioning form forwardly positioned portions, i.e. front side panel extension pieces, of an adjacent further backsheet piece (not shown). A reorientation of partially separated portions may be achieved by rotating the partly separated portions around a y-directionally oriented axis 305 corresponding to the line 308 connecting these to the web, as can be further explained by referring to FIG. 10, depicting a similar set up as shown in FIG. 3. However, the partially separated portions 300 as separated on separation unit 200 remain connected to the web preferably at their trailing end 308, whilst their leading portion 302 is temporarily attached to the transfer unit 230, such as may be achieved by conventional attachment means, such as vacuum suction. At further movement of the web along its web path, the originally leading edge 302 will be pulled away from the transfer unit, optionally supported by appropriate means such as stopping vacuum suction, even when the transfer unit is operated at a matched speed relative to the separation and combination unit. The original trailing end of the separated portion is now forming a fold line to rotate the partially separated portion around a y-directionally extending axis, and the originally leading portion will now rest machine directionally offset relative to its original position and the pattern of the separation line. Thus, when the web with the overfolded partially separated portion reaches the combining unit 600, the original leading portion 302 is now a trailing portion 302', and the original trailing edge 308 is now the leading edge 308'.

Figure 6:
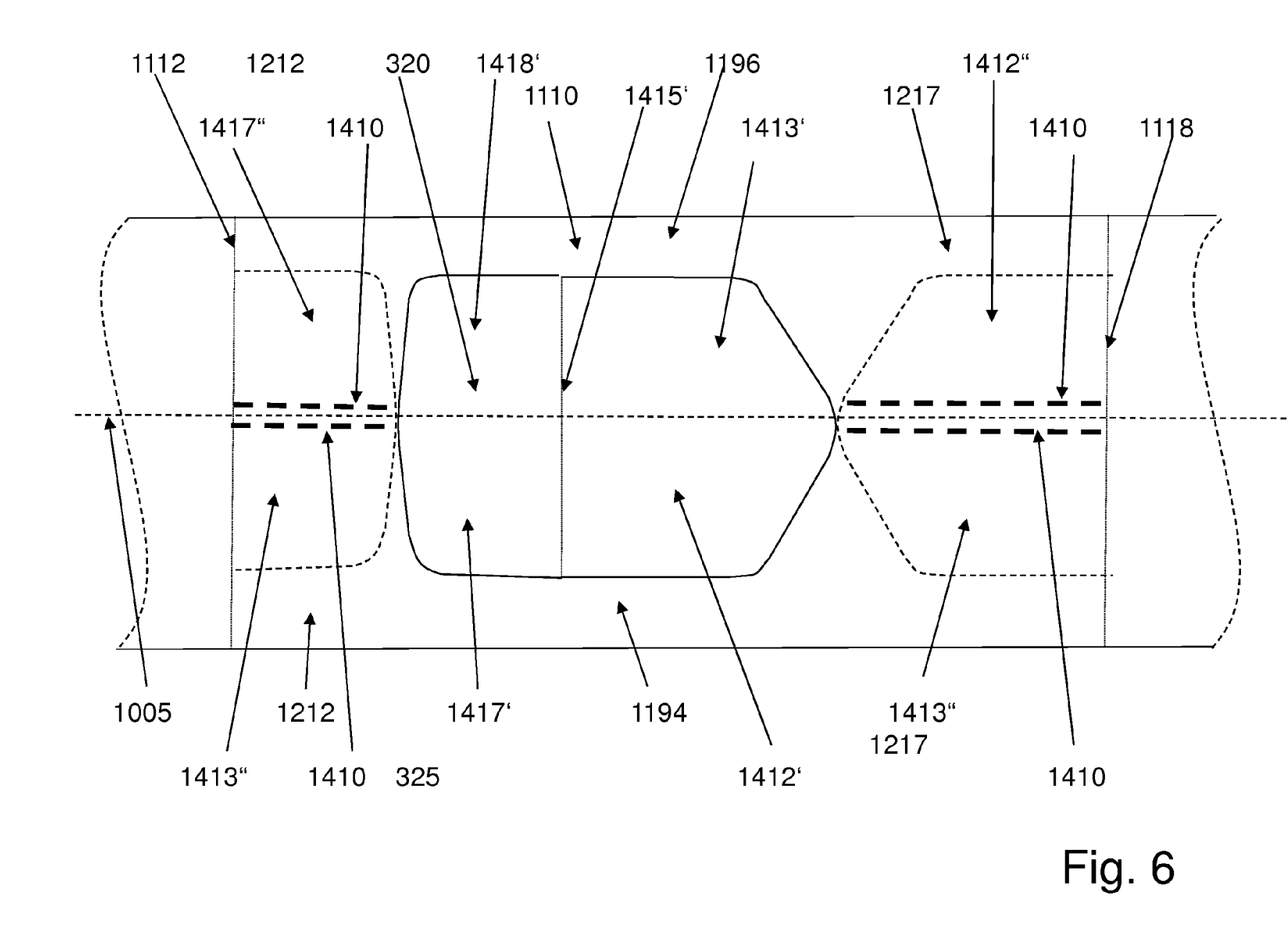
FIG. 6 depicts schematically an execution wherein essentially all of the offcut is used.
Figures 7A, 7C:
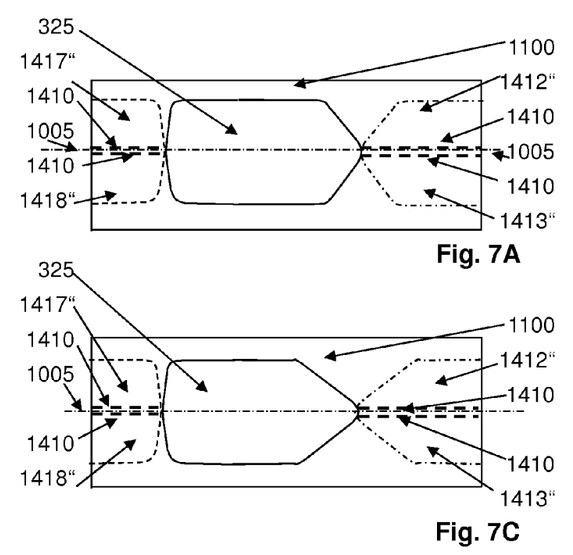
FIG. 7A to 7F depict schematically various executions for waste-free designs.
Figure 7B:
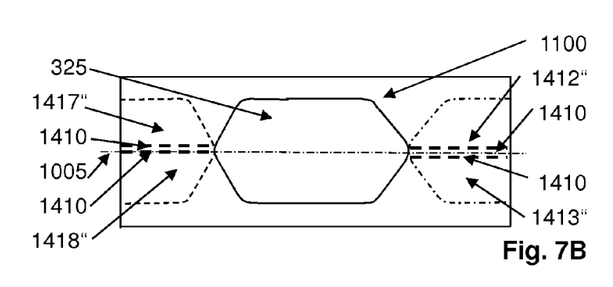
Figure 7D:
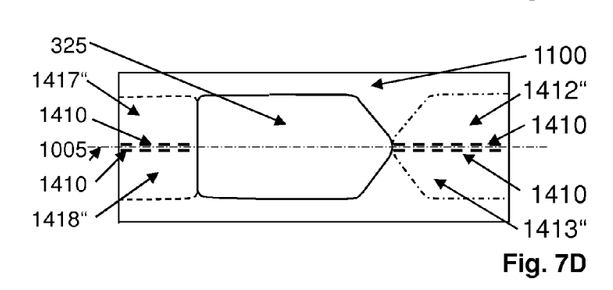
Figure 7E:
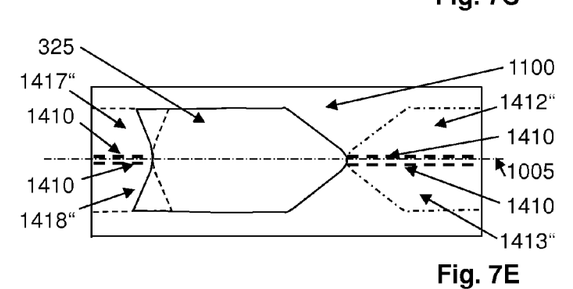
Figure 7F:
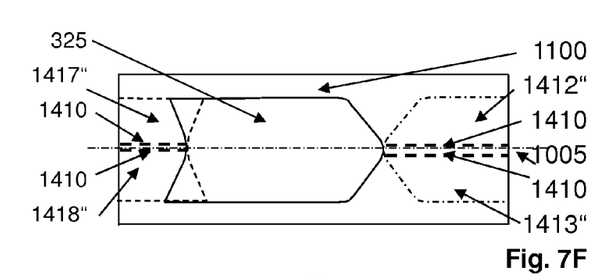
Figures 8, 8B:
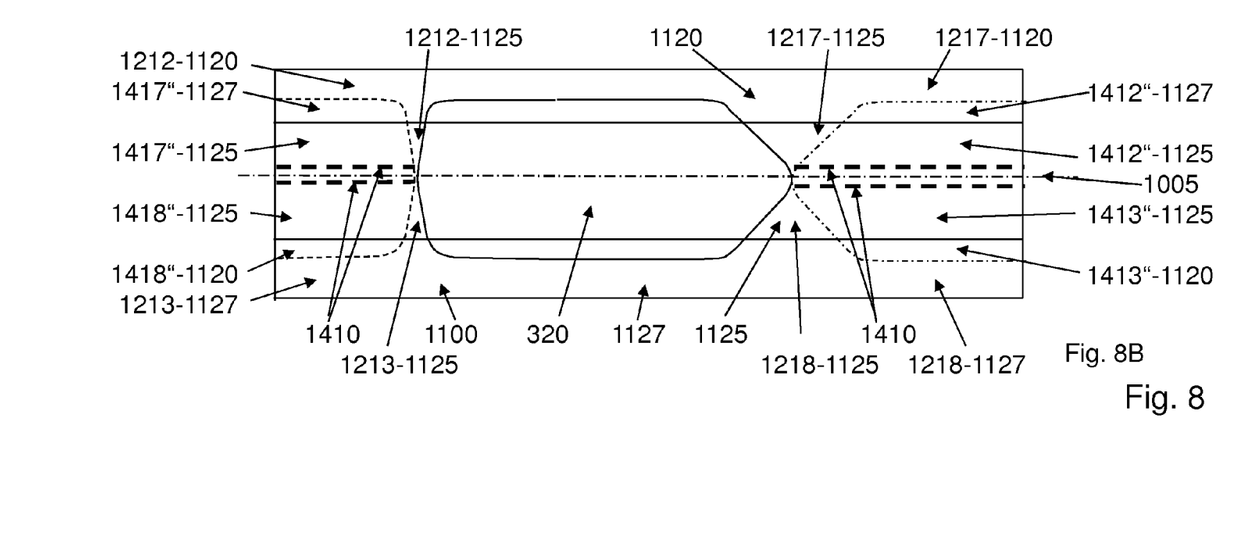
FIG. 8 depicts schematically an execution with a web material comprising elastic and non-elastic sub-webs.
Figure 8A:
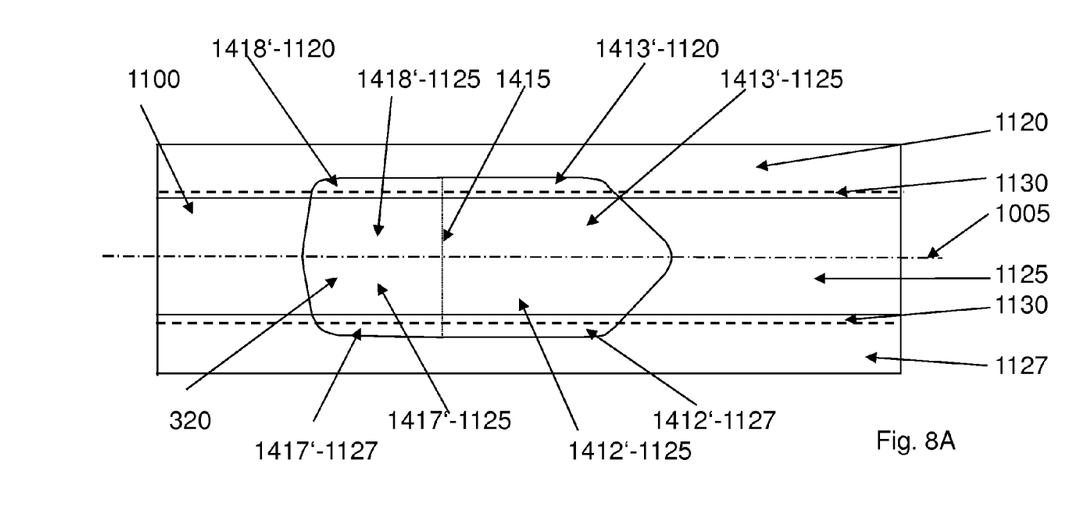

As shown in FIG. 5, the inside portion does not exactly match the shape of the four side panel extensions, a small amount of trim 325 may be removed as described in the above. A more preferred execution avoiding any trim waste is depicted in FIGS. 6 and 7A to F. the same principles of repositioning as described in the context of FIG. 5 apply, except that the contour of the inward portion 320 matches the joint contour of the four sub-portions that form the respective side panel extension pieces. Thus, a continuous web material, as may be represented by a further backsheet 1100, exhibits a first, e.g. a front, margin 1112 and a second, e.g. a rear, margin 1118 that may correspond to a front or rear end margin of a web material piece, a longitudinal centre line 1005, four side panel regions 1212, 1213, 1217, and 1218, as well as two leg hoop regions 1194 and 1196. An inward piece 320 comprises and coterminates with the outer perimeter of the four sub-portions 1412', 1413', 1417', and 1418' for forming the side panel extension pieces. The outer perimeter of these four portions prior to the separation is shown as a solid line coinciding with the demarcation of the inward piece 320, and the four sub-regions are shown separated by the imaginary longitudinal centre line 1005 and a cross-directionally extending imaginary separation line 1415. They are further shown in their post reposition location as side panel extension pieces 1412", 1413", 1417", and 1418", respectively, with thin dashed lines. Connecting lines 1410 (thick dashed lines) connect the side panel extensions to the side panels. Also in this case, a reorientation achieved e.g. by an additional 180° rotational move around a z-directional axis of the cut out piece on the transfer unit. A skilled person will readily realize that, when measuring along the longitudinal centre line 1005, the length of the inward piece 320 corresponds to the sum of the lengths between the inward piece and the first and second, e.g. front and rear, margins of the web material piece 1112 and 1118, respectively. This relation also applies to various different exemplary, non-limiting executions for the shapes for the inward piece 320 as well as side panel extension pieces in their post reposition location 1412", 1413", 1417", and 1418", as shown in FIG. 7A to E. FIGS. 8A and B depict schematically a further execution of the present invention. In FIG. 8A, a web material 1100, as may be a further backsheet material as described in the above, comprises sub-webs here shown with three sub-webs 1120, 1125, and 1127 as may be a unitary web exhibiting differing properties for the different sub-webs, or as indicated in the figure, sub-webs may be positioned longitudinally aligned such that in a small longitudinally extending overlap area (not shown) a longitudinal web connecting is applied, here shown exemplarily as connecting lines 1130. The same principles as described in the context of FIG. 5, 6, or 7 are applied, and sub-portions demarcated by the longitudinal centre line 1005 and the separation line 1415 are separated from said web material and repositioned. Thus, the sub-portions 1412', 1413', 1417', and 1418', separated by along the longitudinal centre line as well as the separation line 1415 comprise sub-regions corresponding to the sub-webs from which they are separated, denoted in FIG. 8A as 1412'-1125 (i.e. sub-region of the sub-portion 1412' comprising the material of the sub-web 1125), 1412'-1127, 1413'-1125, 1412'-1120 and so on. In FIG. 8B, the sub-portions are shown repositioned with respective sub-regions denoted accordingly. Thus, the sub-portion 1412"-1127 corresponds to the repositioned portion 1412, which is made from the sub-web material 1127, and so on.

Figure 9:
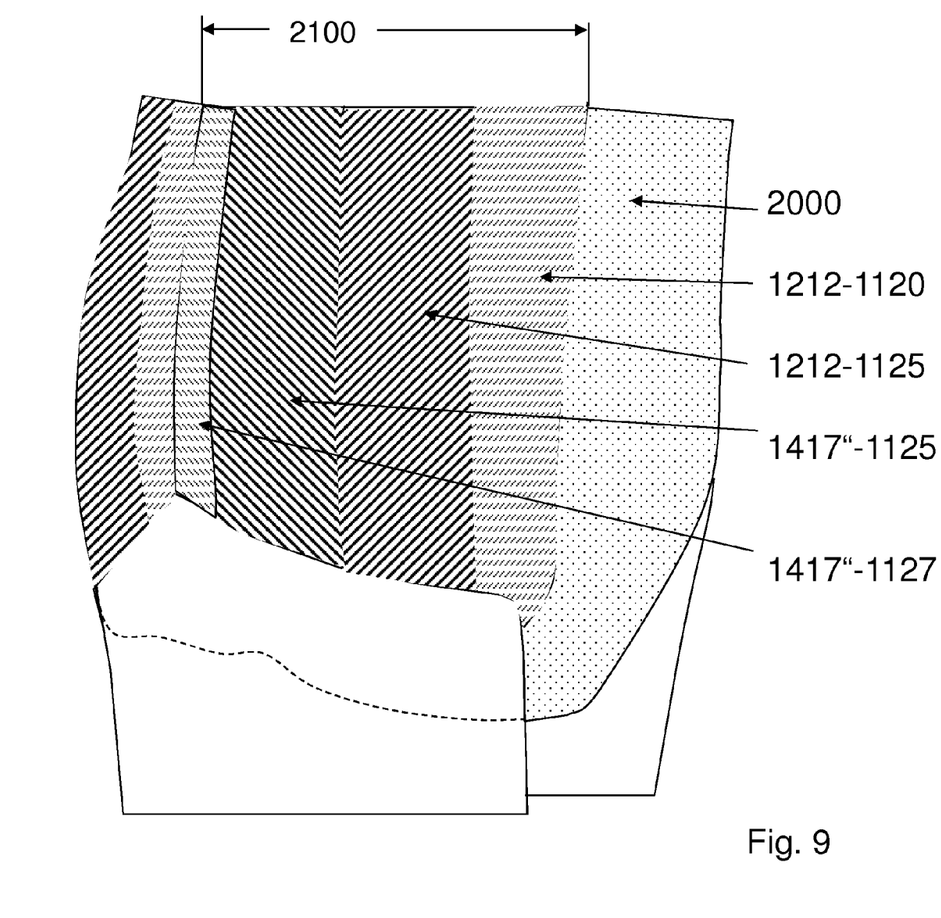
FIG. 9 depicts schematically a perspective view of a disposable article according to the present invention.

In a particular execution, the sub-webs are selected such that a centre portion 1125 is a non-elastic web, whilst two laterally outwardly positioned sub-webs exhibit cross-directional elastic properties. Such an arrangement is particularly useful for an application in a closed pant diaper, as schematically depicted in a perspective view of an in-use configuration. Therein, a combined side panel—side panel extension composite 2100 is connected to a centrepiece material 2000, as may be the front right part in the total pant article, with numerals corresponding to FIG. 8B.

The invention claimed is:
1. Method for repositioning and recombining separated portions of a web material machine-directionally offset,
said method comprising the steps of:
1) providing
a. a web material exhibiting lateral side margins;
b. a separation unit for forming at least partially separated portions in predetermined regions of said web material;
c. a transfer unit for transferring said at least partially separated portions of said web material;
d. a web guide unit for said web material;
e. a combination unit;
2) feeding said web material along a first web path to said separation unit;
3) applying an essentially continuous separation line, thereby creating a series of at least partially separated portions in predetermined regions of said web material in said separation unit,
such that said web material remains essentially continuous along its side margins,
whilst the at least partially separated portions of said web material are circumscribed by said essentially continuous separation line or an essentially cross-directionally extending connection and fold fine that connects end points of said separation line;
4) guiding said web material by said web guide unit along a second part of said essentially continuous web path from said separation unit to said combining unit;
5) transferring at least a leading portion of said at least partially separated portions by said transfer unit along a separated portions path, differing from said second part of said web path;
6) recombining said web material and separated portions in said combination unit;
whereby in said method said separated portions are positioned machine-directionally offset relative to said predetermined regions from which they are separated.

2. A method according to claim 1, wherein said at least partially separated portions are fully separated portions and wherein said method further comprises the steps of
1f) providing a reorientation unit for said fully separated portions;
7) reorienting said fully separated portions along said separated portions path.

3. A method according to claim 1, wherein in said step 6) said separated portions are combined with said web material such that they are positioned cross-directionally offset relative to said predetermined regions.

4. A method according to claim 1, wherein said at least partially portions are partially separated portions and wherein in step 5)
said leading portion of said partially separated portion is temporarily attached to said transfer unit,
wherein further a fold line is created at the trailing edge of said separated portions, and
wherein said partially separated portion is released from said transfer unit and positioned on said web material after being rotated around a y-directionally extending axis.

5. A method according to claim 1, further comprising the steps of
8) providing a further material;
9) combining said further material with said separated portions or said web material such that it contacts either of said materials or both.

6. A method according to claim 1,
further comprising the steps of
1 g) providing a connection unit;
10) connecting said separated portions to said web.

7. A method according to claim 6, wherein in said step 10 said separated portion are connected to said web by melt fusion bonds.

8. A method according to claim 7, wherein said melt fusion bonds are ultrasonically formed bonds.

9. A method according to claim 1, wherein at least two units selected from the group consisting of the transfer unit, the separation unit, the reorientation unit, the combination unit, and the connection unit are essentially unitary.

10. A method for the manufacture of disposable absorbent articles comprising the method for repositioning and recombining separated portions of a web material machine-directionally offset according to claim 1.

11. A method according to claim 10, wherein said separated portions are side panel pieces adapted to form a waist hoop during use.

* * * * *